US010368946B2

(12) United States Patent
Graumann et al.

(10) Patent No.: US 10,368,946 B2
(45) Date of Patent: Aug. 6, 2019

(54) METHOD FOR DETERMINING A TARGET POSITION FOR A MEDICAL PROCEDURE

(75) Inventors: Rainer Graumann, Hoechstadt (DE); Gerhard Kleinszig, Forchheim (DE); Martin Ringholz, Erlangen (DE)

(73) Assignee: Siemens Aktiengesellschaft, Munich (DE)

(*) Notice: Subject to any disclaimer, the term of this patent is extended or adjusted under 35 U.S.C. 154(b) by 701 days.

(21) Appl. No.: 14/112,951

(22) PCT Filed: Apr. 13, 2012

(86) PCT No.: PCT/EP2012/056744
§ 371 (c)(1),
(2), (4) Date: Oct. 21, 2013

(87) PCT Pub. No.: WO2012/143290
PCT Pub. Date: Oct. 26, 2012

(65) Prior Publication Data
US 2014/0051994 A1 Feb. 20, 2014

(30) Foreign Application Priority Data

Apr. 20, 2011 (DE) ........................ 10 2011 007 796

(51) Int. Cl.
*A61B 6/00* (2006.01)
*A61B 34/10* (2016.01)
(Continued)

(52) U.S. Cl.
CPC .............. *A61B 34/10* (2016.02); *A61B 6/032* (2013.01); *A61B 6/12* (2013.01); *A61B 6/4085* (2013.01);
(Continued)

(58) Field of Classification Search
CPC ....... A61B 19/5244; A61B 6/032; A61B 6/12; A61B 6/4085; A61B 6/4441; A61B 19/50;
(Continued)

(56) References Cited

U.S. PATENT DOCUMENTS 6,317,616 B1 * 11/2001 Glossop ................. A61B 90/10
600/407
7,876,942 B2    1/2011 Gilboa
(Continued)

FOREIGN PATENT DOCUMENTS

DE    102005044033 A1    3/2007
WO    2007031314 A2    3/2007
(Continued)

*Primary Examiner* — Jonathan Cwern
(74) *Attorney, Agent, or Firm* — Laurence Greenberg; Werner Stemer; Ralph Locher

(57) ABSTRACT

A method for determining the location, in a coordinate system, of a target position for an invasive medical procedure on a patient. An entry mark that defines the coordinate system and indicates an entry position for the procedure is affixed to the patient. A site marker, which can be identified in a radioscopy image, is fixed in a known relative location in the coordinate system. At least two 2D radioscopy images of the patient, which both depict the respective site marker and the target position, are recorded from different recording directions. The location of the target position in the coordinate system is determined from the representation of the target position and from the representation of the site marker in the 2D radioscopy images and from the relative location of the site marker in the coordinate system.

5 Claims, 3 Drawing Sheets

(51) Int. Cl.
*A61B 6/03* (2006.01)
*A61B 6/12* (2006.01)
*A61B 34/20* (2016.01)
*A61B 90/00* (2016.01)

(52) U.S. Cl.
CPC ............ *A61B 6/4441* (2013.01); *A61B 34/20* (2016.02); *A61B 2034/107* (2016.02); *A61B 2034/2055* (2016.02); *A61B 2090/376* (2016.02); *A61B 2090/3966* (2016.02); *A61B 2090/3983* (2016.02)

(58) Field of Classification Search
CPC ...... A61B 2019/5483; A61B 2019/507; A61B 2019/5466; A61B 2019/5238; A61B 2019/5255
See application file for complete search history.

(56) References Cited

U.S. PATENT DOCUMENTS

| | | | |
|---|---|---|---|
| 2008/0125846 A1* | 5/2008 | Battle | A61B 5/06 623/1.11 |
| 2008/0221520 A1 | 9/2008 | Nagel et al. | |
| 2009/0171184 A1 | 7/2009 | Jenkins et al. | |

FOREIGN PATENT DOCUMENTS

| | | | |
|---|---|---|---|
| WO | 2007113815 A2 | 10/2007 | |
| WO | 2010145975 A1 | 12/2010 | |

* cited by examiner

METHOD FOR DETERMINING A TARGET POSITION FOR A MEDICAL PROCEDURE

CROSS-REFERENCE TO RELATED APPLICATION

This is a § 371 national stage of copending international application No. PCT/EP2012/056744, filed Apr. 13, 2012, which designated the United States; this application also claims the priority, under 35 U.S.C. § 119, of German patent application No. 102011007796.0, filed Apr. 20, 2011; the prior applications are herewith incorporated by reference in their entirety.

BACKGROUND OF THE INVENTION

Field of the Invention

The invention relates to a method for determining the location, in a coordinate system, of a target position for an invasive medical procedure on a patient.

Invasive medical procedures are performed on patients. A medical instrument herewith penetrates the skin of the patient at an entry position, e.g. a specific position on the surface of the stomach of the patient. From there it is to reach a target position inside of the patient. The target position is then a specific point inside of the patient, e.g. his/her gallbladder.

In order to introduce the instrument as accurately as possible in respect of the target position, a method by the company ActiViews, Haifa, Israel is known for instance. This method is based on a small video camera, which is clipped to needle-shaped instruments, for instance biopsy needles or K-wires. The entry position for the instrument is the puncture site on the surface of the body. A marker film, which has both visual markers and also x-ray markers, is glued to the patient at the puncture site. The position and orientation of the video camera and thus of the instrument is determined in real-time in the image recorded by the camera using the representation of the optical markers. Since the marker film is positioned at the planned puncture site, to ensure global and uniform consistency, curvatures of the needle can be measured by way of the video camera for instance and are taken into account in terms of guiding the instrument to the target position in the patient. The camera, together with the optical markers, herewith forms an optically operating navigation system for the movement of the instrument.

A 3D CT recording of the patient is acquired for implementation of the method in a first step and thereupon an intervention plan is performed on the patient. In other words, both the target position and also the entry position is defined with the aid of the 3D CT recording in relation to the patient, i.e. to his/her anatomy. In a second step, the marker film is then positioned in a defined manner at the planned entry point on the patient.

A further 3D CT data record is then produced of the patient with a fixed marker film, which represents both the marker film and/or the x-ray marker and also the target position in terms of its reconstruction volume. The x-ray markers present on the marker film are identified in the 3D CT data record and assigned to a corresponding coordinate system or reference system, which is defined by the marker film. In other words, the assignment of the coordinate systems to the optical markers and the x-ray markers thus takes place. The assignment of the target position which is visible in the 3D CT data record to the coordinates of the optical navigation system is thus also possible. With this method, a transformation is calculated between the patient, the x-ray markers, the optical markers and the instrument. The target location or target position is then known in the coordinate system of the optical markers, which also serves for the navigated guidance of the instrument to the target position.

The disadvantage with the method is that two preoperative 3D CT data records have to be generated. An x-ray method with a sufficiently large reconstruction volume is required at least for the second 3D data record, since the markers on the marker film on the body surface and the target position in the patient have to be represented in the same 3D CT data record. It is further disadvantageous that the patient wears the marker film during the period of time between the two preoperative CT recordings until the operation on the skin. Possible skin displacements can thus not be measured or corrected by the method. A simple and cost-effective intraoperative 2D imaging can not be included in the method, since its reconstruction volume is often too small.

BRIEF SUMMARY OF THE INVENTION

The object of the present invention is to specify an improved method for determining the position of an afore-cited target position in a coordinate system.

The object is achieved by a method as claimed.

The inventive method is based on the entry position and the target position in the patient already having been determined or defined preoperatively or intraoperatively defineable e.g. using x-rays, in relation to his/her anatomy. This can take place in any manner, e.g. by preceding MR or ultrasound examinations or the afore-cited 3D CT image data record.

As explained above, an entry mark is firstly fixed to the patient. This defines a coordinate system and also clearly shows the entry position for the invasive medical procedure on the patient. The location of the entry position in the coordinate system is defined by the entry marker and thus, since this defines the coordinate system, the relative position of the entry position in the coordinate system is also known.

In a next step, a site marker which can be identified in a radioscopy image is fixed in a known relative position in the coordinate system. In accordance with the invention at least two 2D radioscopy images of the patient, which together represent the site marker and the target position in each instance, are subsequently recorded from different recording directions. The location of the target position in the coordinate system is then determined from the representation of the target position and the site marker in the two radioscopy images and the known relative position of the site marker in the coordinate system.

In other words, the afore-cited known method is extended in accordance with the invention such that this can be used exclusively on the basis of intraoperative 2D x-ray images. The invention is herewith based on the knowledge that the use of 2D x-ray images instead of a 3D CT data record requires that the recording geometry of the radioscopy device, which generates the 2D radioscopy images, is known for both recordings. This can take place for instance in that the site markers are attached at any point in time, even without the patient, provisionally in the radiation path of the radioscopy device and the projection matrices of the radioscopy system are calculated herefrom. The marker geometry only needs to be suited to such a determination.

According to the invention, it is then advantageous that exclusive use of 2D imaging methods and/or radioscopy methods intraoperatively is sufficient to determine the location of the target position in a coordinate system for a procedure on a patient.

In accordance with the invention, the site marker contains marker structures such as circles, stars or triangles which can be clearly identified in the 2D radioscopy images i.e. distinguished individually in each instance. Individual marker structures of the site marker can thus be clearly identified in the radioscopy image or for instance segmented automatically by means of image evaluation.

The two different recording directions for the 2D radioscopy images must only be selected such that a site assignment of the respective image contents in a three-dimensional coordinate system is possible from the totality of both images. Radioscopy images are ideally recorded for instance from projection directions which are orthogonal to one another. It must only be ensured here that an orthogonal recording, e.g. a marker plate, records directly one from side. The projection directions are thus to be selected as orthogonally as possible, with the boundary condition of marker recognizability.

In the simplest and most usual case, the 2D radioscopy images are x-ray images, the site markers are then x-ray markers. The radioscopy device is an x-ray device, e.g. an x-ray C-arm which is generally available in an operating theatre.

In a preferred embodiment of the invention, a radioscopy device is fixed in a 3D recording position. This defines a fixed basic position. In the case of an x-ray C-arm, its base support is firstly aligned in a specific position with respect to the patient. A set of 2D projection images of the patient is produced from this position with the aid of the radioscopy device. To this end, the radioscopy device is aligned in different recording directions in one and the same 3D recording position. In the example of the x-ray C-arm, this takes place by orbital pivoting of the C-arm in the case of a stationary base support. The 2D projection images are recorded such that these are used to reconstruct 3D image data. Contrary to the above, the 3D image data nevertheless contains the target position but not the site markers. In this embodiment of the invention, the 2D radioscopy images are then recorded with the same radioscopy device in an unchanged 3D recording position.

In other words, 3D image data of the patient is therefore intraoperatively generated, which comprises a comparatively small reconstruction volume. This is generally only sufficient to represent the target position, but not also to simultaneously represent the site marker. 3D image data of this type is therefore not suited to the known method of location determination. According to the invention, the 2D radioscopy images are however recorded with one and the same radioscopy device, said 2D radioscopy images then (contrary to the reconstruction volume) being selected so that they represent both the site markers and also the target position in 2D radioscopy images from two different recording directions.

In one variant of this method, two of the 2D projection images are used as 2D radioscopy images. In other words, two of the images of the image data record used for 3D reconstruction, in other words part of the 2D projection images is used twice, namely both to reconstruct the 3D volume and also for the inventive method for determining the location of the target position.

In a preferred embodiment of the method, a film is fixed on the patient as an entry mark. This then supports the site marker for instance, such as also in the known method.

In a preferred embodiment of the invention, the coordinate system is assigned to a navigation system. The navigation system is used for navigation, in other words targeted guidance, of an instrument, with which the invasive medical procedure is to be performed on the patient. A navigation marker of the navigation system is then arranged in a known relative position in respect of the entry marker. A navigation device detecting the navigation marker is arranged in a known relative position in respect of the instrument and the site marker is arranged in a known relative position in respect of the navigation device. The instrument can be guided through the entry position to the target position in the position with the aid of the navigation system.

In this embodiment of the method, the relative position of the site marker is therefore determined in the coordinate system by the navigation system and is herewith known in the method.

In order to configure the afore-cited known relative positions as simply as possible, in a preferred embodiment, the navigation marker is then fixedly attached to the entry mark, the site marker is fixedly attached to the navigation device and the navigation device is fixedly attached to the instrument. The respective relative positions are thus clearly defined and easily determinable.

In the event of an optically operating navigation system, the navigation markers are optical markers and the navigation device is a camera.

In a preferred embodiment, additional radioscopy image data of the patient is recorded in advance, in other words prior to starting the first inventive method step, in order to define the target position and the entry position relative to the patient. 2D images from different recording directions may also be sufficient here. Alternatively however a number of 2D projections and/or x-ray images or also a preoperative 3D image data record according to the prior art can however also be produced.

BRIEF DESCRIPTION OF THE SEVERAL VIEWS OF THE DRAWING

For a further description of the invention, reference is made to the exemplary embodiments of the drawings, in which, in a schematic basic diagram in each instance.

DESCRIPTION OF THE INVENTION

Figure 1:
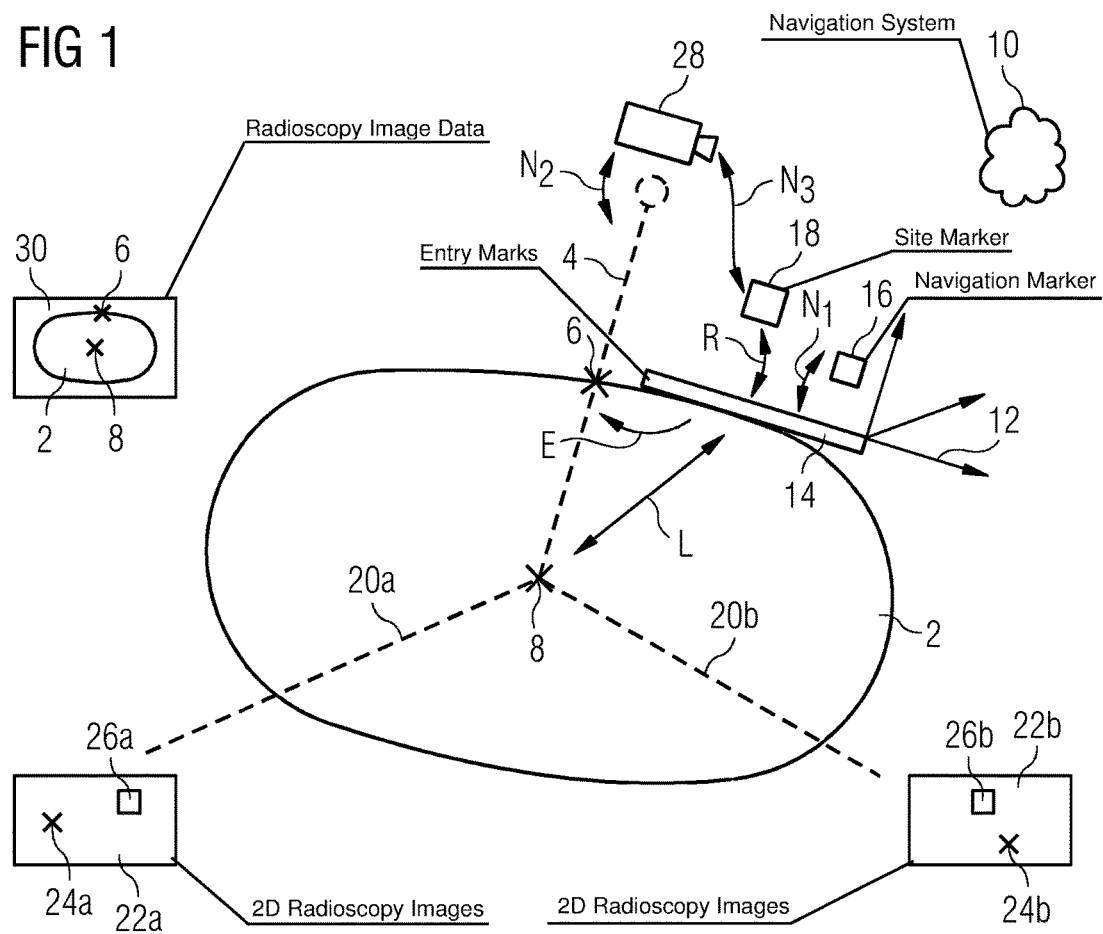
FIG. 1 shows the implementation of the inventive method on a patient.

FIG. 1 shows a patient 2, on which an invasive medical procedure is to be implemented. To this end, an instrument 4 is to be introduced through an entry position 6 on the body surface of the patient 2 to a target position 8 inside of the patient 2. Both the entry position 6 and also the target position 8 is firstly defined in a preoperative step in terms of its relative position in respect of the patient 2 or in respective of his/her anatomy. This takes place for instance by recording a preoperative, high-resolution MR image data record, the recording of x-ray images, ultrasound examinations, etc. The medical procedure on the patient is to take place with the aid of a navigation system 10 only indicated in FIG. 1. A coordinate system 12 is therefore assigned to the navigation system 10.

An entry mark 14 in the form of a film which can be glued to the patient 2 or his/her body surface is firstly fixed to the patient 2. The entry mark 14 defines the coordinate system 12, e.g. by means of optically detectable navigation markers 16 attached thereto in a known relative position and associated with the navigation system 10. In a simplest way, these are arranged directly on the film.

The entry mark 14 also indicates the entry position 6, is placed for instance at a known distance and alignment in respect of the same on the patient 2. The relative position E of the entry position 6 with respect to the entry mark 14 and thus in the coordinate system 12 is thus known and shown symbolically in FIG. 1 by an arrow.

In a next step, a site marker 18, likewise in a known relative position R, symbolized by an arrow, is positioned with respect to the coordinate system 12 or the entry mark 14. Its position in the coordinate system 12 is thus also known.

Two 2D radioscopy images 22a, b of the patient 2 are now recorded in two different recording directions 20a, b. The example shows x-ray images, the recording directions 20a, b symbolize the spatial direction of the central beam of an x-ray system (not shown). The recording directions 20a, b are selected here such that the target position 8 and also the entry position 6 are detected in each instance in both 2D radioscopy images 22a, b. The site marker 18 is embodied such that this can be reproduced in the radioscopy images 22a, b, these therefore contain representations 24a, b of the target position 8 and representations 26a, b of the site marker 18.

In accordance with the invention, the location L, indicated in FIG. 1 again by an arrow, of the target position 8 is determined in the coordinate system 12 from the representations 24a, b of the target position 8 and the representations 26a, b of the site marker 18 and the relative position R of the site marker 18 in the coordinate system 12. One prerequisite here is the knowledge of the recording geometry of the respective 2D radioscopy images 22a, b, i.e. the knowledge of the spatial position of the recording directions 20a, b and the respective projection matrices of the representations in the coordinate system 12.

If the instrument 4 is now likewise detected in the navigation system 10, on account of the knowledge of all position data in the coordinate system 12, the instrument 4 can be guided accurately in terms of target through the entry position 6 to the target position 8.

In order to determine the relative position R of the site marker 18 in the coordinate system 12, the navigation marker 16 can be used in particular if this is placed in a known relative position N1, shown in FIG. 1 by an arrow, in respect of the entry mark 14. A navigation device 28 of the navigation system 10 detecting the navigation marker 16, e.g. a camera in the case of an optical mark as navigation marker 16, is then likewise arranged in a known relative position N2 in respect of the instrument 4, indicated in FIG. 1 by an arrow. In this case, the site marker 18 is then attached in a known relative position N3 in respect of the navigation system 28. The relative position R in the coordinate system 12 can then be determined by the navigation system 10 with the aid of the known relative positions N1-3. In other words, the relative position R in the coordinate system 12 is known a priori, but is instead firstly determined by the navigation system 10.

In an alternative embodiment of the method, additional radioscopy image data 30 of the patient 2 is recorded prior to its start in order to define the respective location of the target position 8 and the entry position 6 in the patient 2 relative to the patient 2 or his/her anatomy.

FIG. 2 once again shows the patient 2 with an attached entry mark 14 and positioned instrument 4. The entry mark 14 herewith directly specifies the entry position 6, by the latter lying directly in the region of the entry mark 14, the instrument 4 in other words punctures the entry mark 14 at a defined. Furthermore, in the exemplary embodiment according to FIG. 2, the navigation markers 16 are pressed as optical markers directly onto the entry mark 14. The navigation device 28 in the form of a camera is fastened directly on the instrument 4. Furthermore, the navigation device 28 supports the site marker 18 fixedly installed hereupon in the form of x-ray markers. The two 2D radioscopy images 22a, b are recorded here with the aid of a radioscopy device 32, in the example an x-ray C-arm. To this end the C-arm is pivoted from the shown position of the recording direction 20a in the direction of the arrow 34 into a second recording direction 20b (shown with a dashed line). In this embodiment, x-ray markers in the form of site markers 18 are attached to the video camera in the form of the navigation device 28, said x-ray markers enabling determination of the coordinate transformation between the 2D radioscopy images 22a, b supplied by the radioscopy device 32 and the video image supplied by the navigation device 28 and thus the surgical instrument 4.

It is adequate in this case if the marker film, in the form of the entry mark 14, only contains optical markers in the form of the navigation marker 16. Alternatively, the transformation can also take place by way of the marker film, in other words entry mark 14, if the site markers 18 are additionally arranged there. Site markers 18 are then no longer required on the navigation device 28.

In the two radioscopy images 22a, b recorded as orthogonally as possible, i.e. with recording directions 20 a, b which are as orthogonal as possible, the respective representations of target position 8 and entry position 6, as explained in conjunction with FIG. 1, are identified. It is therefore necessary for the x-ray geometry for both 2D radioscopy images 22a, b to be known, this can take place for instance in that the entry mark 14 is provisionally attached to any object at any point in time and the projection matrices are calculated from their x-ray recordings.

The entry mark 15 is then glued there after defining the entry position 6 and as described above, the two x-ray recordings 22a, b are acquired and the location L of the target position 8 in the coordinate system 12 of the entry mark 14 is determined. The instrument 14 in the form of the needle can now be guided to the target position 8 exclusively on the basis of the optical images of the marker film or navigation marker 16 generated by the navigation device 28, wherein needle curvatures can be determined and corrected as in the known method.

Figure 2:
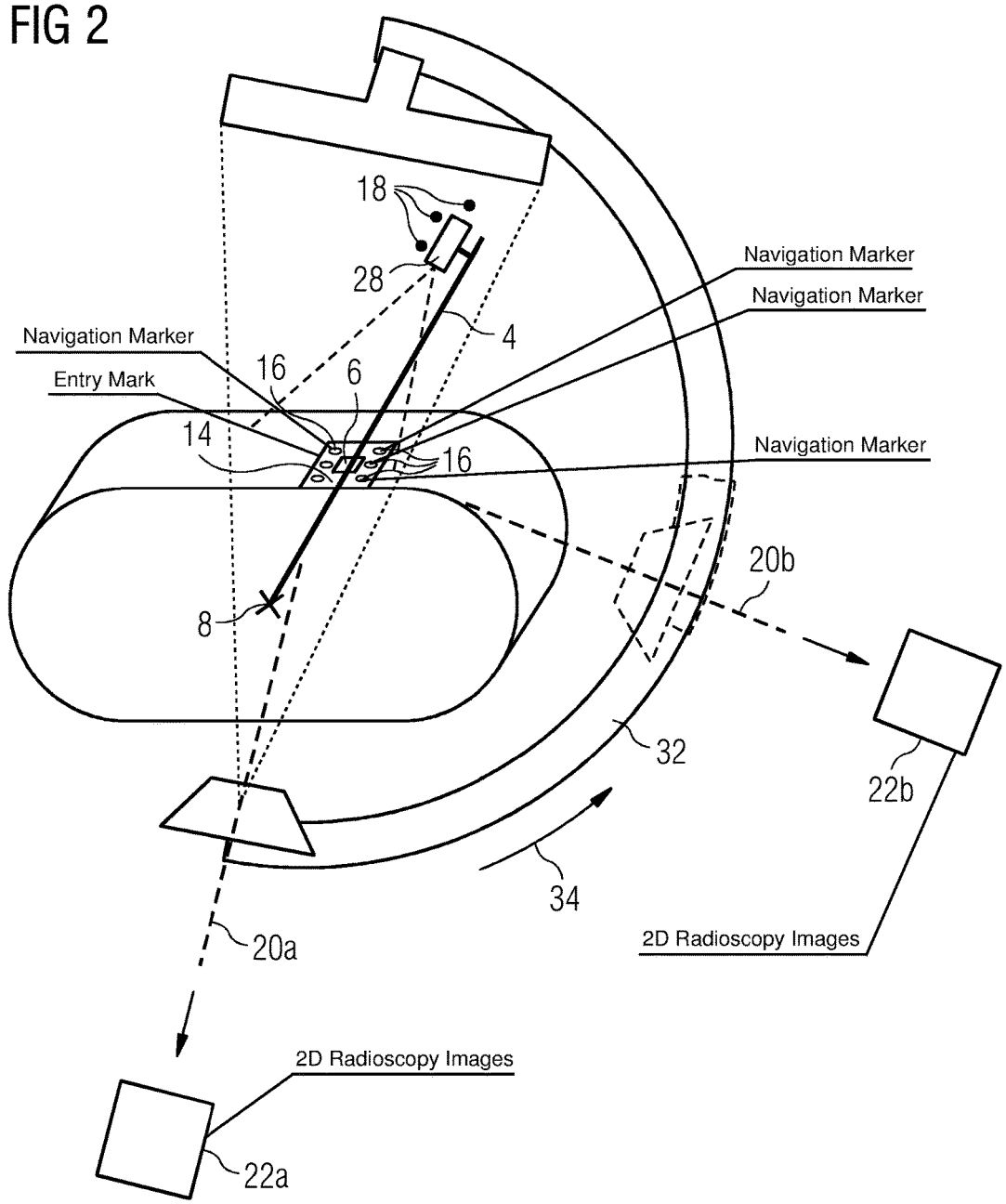
FIG. 2 shows the patient from FIG. 1 with an x-ray C-arm.
Figure 3:
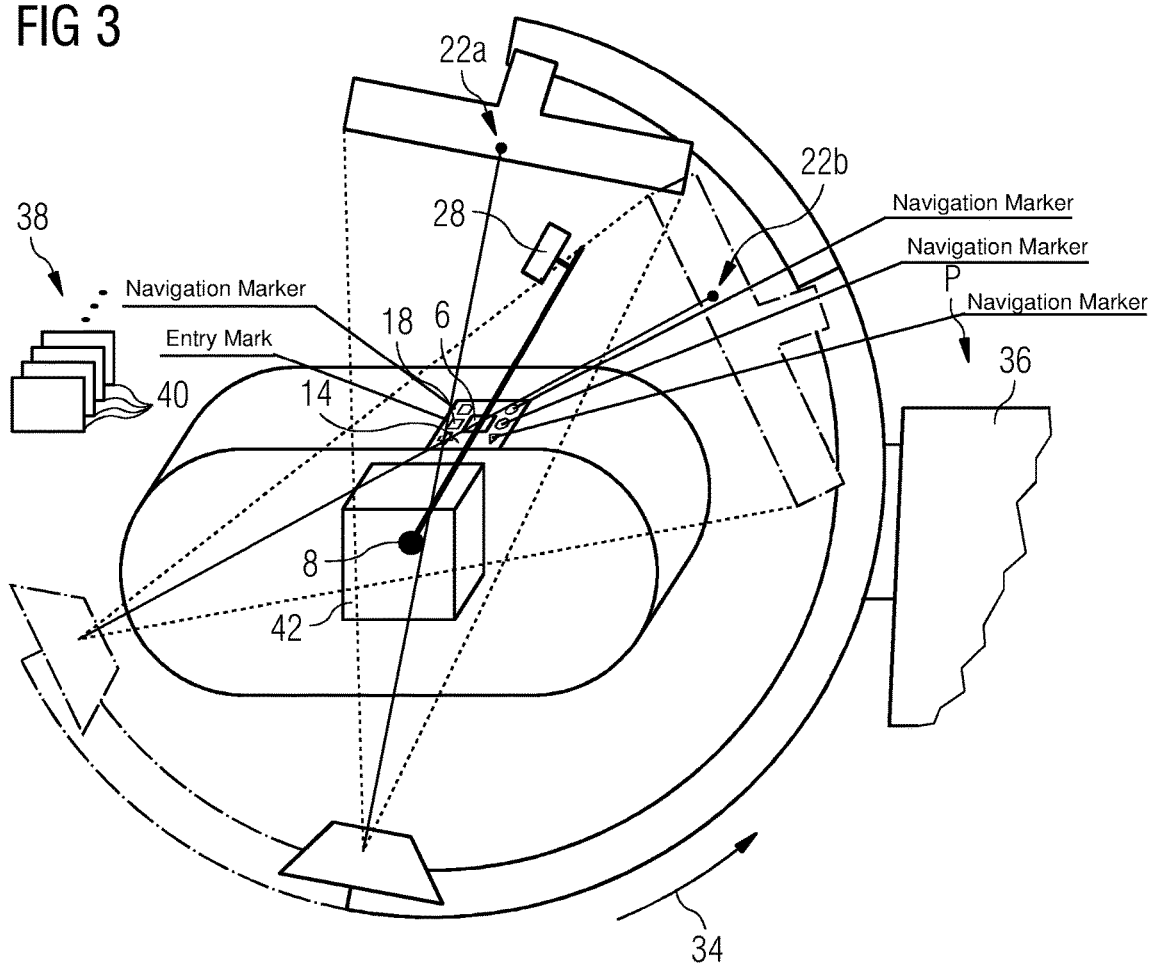
FIG. 3 shows the patient from FIG. 1 during a 3D x-ray imaging.

FIG. 3 shows an alternative embodiment, in which, contrary to FIG. 2, the site markers 18 are arranged directly on the entry mark 14 in the form of x-ray markers. The navigation device 28 therefore does not support any site markers 18. The relative position R of the site markers 18 in the coordinate system 12 of the entry mark 14 is known, since these are fixedly arranged in the known position.

FIG. 3 shows the radioscopy device 32 with its base support 36 fixedly positioned in a 3D recording position P. The base support 36 is firstly no longer moved. Only the actual C-arm of the radioscopy device 32 is moved in or counter to the direction of the arrow 34, in order to record a set 38 of 2D projection images 40. 3D image data 42 is reconstructed from the set 38.

Since this involves intraoperative 3D imaging, the reconstruction volume of the 3D image data 42 is comparatively small, so that this only contains the target position 8 and its immediate vicinity, but not however the entry position 6 and/or the entry mark 14. Nevertheless, according to a variant of the invention in the unchanged 3D recording position P, the radioscopy device 32 is now pivoted again between the two indicated position in order to record the two 2D radioscopy images 22a, b. These are symbolized in FIG. 3 by the respective representation of one of the local markers 18 at the point of the x-ray detector.

In an alternative embodiment of the invention, the 2D radioscopy images 22a, b are now not recorded separately, but two 2D projection images 40 produced already from two different recording directions are already used herefor, which, provided they are suitable, reproduce both the target position 8 and also the site markers 18 respectively.

The intraoperative 3D C-arm imaging only has small reconstructed volumes, so that in the normal case, the site markers 18 attached outside of the patient 2 are not contained in the reconstructed volume and a registration between the instrument and image data record is thus not possible. In FIG. 3, the marker film therefore contains site markers 18 e.g. ellipses, circles, triangles or star-shaped objects, which can be distinguished from one another. These objects can therefore be automatically segmented in the 2D radioscopy images 22a, b, e.g. by means of model-based segmentation. With the aid of the correspondingly known projection matrices, the 3D positions of the x-ray markers are thus determined again from the 2D positions of the projected x-ray markers and/or site markers 18 in the at least two projection recordings 22a, b. The registration of the video camera and thus of the instrument can then take place from the knowledge of the 3D positions of the x-ray markers.

According to FIG. 3, a number of 2D x-ray images or a 3D data record of the patient is firstly generated. The determination of the entry position 6 and target position 8 take place herefrom. The marker film is glued to the patient and the 3D positions or the x-ray markers of the marker film are determined either as described from a 3D data acquisition or from a number of 2D projection recordings so the corresponding projection matrices are known. The registration with the optical video camera and then the guidance of the instrument 4 then takes place with the aid of the navigation system 10.

In this method variant, the exclusive use of intraoperative imaging is sufficient, a preoperative imaging such as CT or MR, which generates the entire patient and not only a correspondingly small volume, is no longer necessary. If correspondingly high quality and large-volume CT or MR images of the patient exist, these can be transmitted for instance via image fusion to the intraoperative 3D C-arm imaging.

An intraoperative 3D C-arm imaging is generally not permitted for diagnosis purposes.

LIST OF REFERENCE CHARACTERS

2 Patient
4 Instrument
6 Entry position
8 Target position
10 Navigation system
12 Coordinate system
14 Entry mark
16 Navigation marker
18 Site marker
20a, b Recording direction
22a, b 2D Radioscopy images
24a, b Representation of the target position
26a, b Representation of the site marker
28 Navigation device
30 Radioscopy image data
32 Radioscopy device
34 Arrow
36 Base support
38 Set
40 2D projection image
42 3D image data
E, R Relative position
L Location
N1, 2, 3 Relative position
P 3D recording position

The invention claimed is:

1. A method for determining a location of a target position for an invasive medical procedure on a patient in a coordinate system, the method comprising:
  recording radioscopy image data of the patient in order to define the target position and an entry position for the procedure, wherein the entry position is on a surface of the patient;
  after recording the radioscopy image data of the patient, affixing an entry mark to the patient defining the coordinate system and indicating the entry position for the procedure;
  after recording the radioscopy image data of the patient, fixing a site marker to be identified in a radioscopy image in a known relative position in the coordinate system;
  after affixing the entry mark to the patient and after fixing the site marker, recording at least two 2D radioscopy images of the patient from mutually different recording directions, each image capturing the site marker and the target position, wherein the different recording directions are substantially orthogonal to each other; and
  determining the location of the target position in the coordinate system from a representation of the target position and a representation of the site marker in the 2D radioscopy images and the relative position of the site marker in the coordinate system.

2. The method according to claim 1, which comprises recording a set of 2D projection images for reconstructing the target position, without recording 3D image data containing the site marker, with a radioscopy device that is fixed in a 3D recording position, wherein the 2D radioscopy images are recorded with the same radioscopy device without changing the 3-D recording position.

3. The method according to claim 2, which comprises using two images in the set of the 2D projection images as 2D radioscopy images.

4. The method according to claim 1, which comprises affixing a film on the patient as an entry mark.

5. The method according to claim 1, wherein:
  the coordinate system is associated with a navigation system used to navigate an instrument performing the procedure;
  a navigation marker of the navigation system is arranged in a known relative position in respect of the entry mark;

a navigation device detecting the navigation marker is arranged in a known relative position in respect of the instrument, wherein the navigation device is part of the navigation system; and the site marker is arranged in a known relative position in respect of the navigation device.

\* \* \* \* \*